United States Patent [19]

Audousset et al.

[11] Patent Number: 5,595,573
[45] Date of Patent: Jan. 21, 1997

[54] KERATIN FIBER DYEING COMPOSITIONS BASED ON A COMBINATION OF OXIDATION DYES AND CORRESPONDING DYEING PROCESSES

[75] Inventors: Marie-Pascale Audousset, Asnieres; Mireille Maubru, Chatou, both of France

[73] Assignee: L'Oreal, Paris, France

[21] Appl. No.: 552,277

[22] Filed: Nov. 2, 1995

[30] Foreign Application Priority Data

Nov. 2, 1994 [FR] France .................................. 94 13081

[51] Int. Cl.$^6$ ....................................................... A61K 7/13
[52] U.S. Cl. .......................... 8/412; 8/406; 8/407; 8/408; 8/409; 8/410; 8/411; 8/416; 8/421
[58] Field of Search ............................... 8/406, 407, 408, 8/409, 410, 411, 412, 416, 421

[56] References Cited

U.S. PATENT DOCUMENTS

| | | | |
|---|---|---|---|
| 4,152,112 | 5/1979 | Bugaut et al. | 8/10.2 |
| 4,268,264 | 8/1981 | Grollier et al. | 8/412 |
| 4,295,848 | 10/1981 | Grollier et al. | 8/412 |
| 4,311,478 | 1/1982 | Bugaut et al. | 8/407 |
| 4,323,360 | 4/1982 | Bugaut et al. | 8/406 |
| 4,330,292 | 5/1982 | Bugaut et al. | 8/406 |
| 4,333,730 | 6/1982 | Bugaut et al. | 8/414 |
| 4,370,142 | 1/1983 | Bugaut et al. | 8/412 |
| 4,396,392 | 8/1983 | Konrad et al. | 8/412 |
| 4,840,639 | 6/1989 | Husemeyer et al. | 8/412 |
| 4,904,275 | 2/1990 | Grollier | 8/411 |
| 5,500,022 | 5/1991 | Cotteret | 8/412 |

FOREIGN PATENT DOCUMENTS

| | | |
|---|---|---|
| 0008039 | 2/1980 | European Pat. Off. . |
| 0459901 | 12/1991 | European Pat. Off. . |
| 2364888 | 4/1978 | France . |
| 2586913 | 3/1987 | France . |
| 3743769 | 7/1989 | Germany . |
| 2239265 | 6/1991 | United Kingdom . |

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

A dye composition for the oxidation dyeing of keratin fibers, which composition contains, as oxidation dye, at least one selected para-phenylenediamine and/or at least one of the salts thereof, and at least 3-methyl-6-aminophenol and/or at least one of the acid-addition salts thereof. The invention also relates to a dyeing process using this composition in the presence of an oxidizing agent.

20 Claims, No Drawings

KERATIN FIBER DYEING COMPOSITIONS BASED ON A COMBINATION OF OXIDATION DYES AND CORRESPONDING DYEING PROCESSES

The present invention relates to dye compositions for the oxidation dyeing of keratin fibers, in particular human keratin fibers such as the hair, containing specific oxidation dyes which are intended to be used in combination with an oxidizing composition.

It is known to dye keratin fibers, and in particular human keratin fibers, with dye compositions containing oxidation dye precursors, in particular ortho- or para-phenylenediamines, and ortho- or para-aminophenols, generally referred to as oxidation bases. The oxidation dye precursors, or oxidation bases, are colourless or weakly-coloured compounds which, when combined with oxidizing products, may give rise, via a process of oxidative condensation, to coloured compounds and dyes.

It is also known that the shades obtained with these oxidation bases may be varied by combining them with couplers or colour modifiers, the latter being chosen in particular from aromatic meta-diamines, meta-aminophenols and meta-diphenols.

The variety of molecules employed as oxidation bases and couplers allows a broad range of colours to be obtained.

The so-called "permanent" dyeing obtained by means of these oxidation dyes must moreover satisfy a certain number of requirements. Thus, it should have no drawbacks from the toxicological point of view, it should allow shades to be obtained in the desired intensity and it should behave well in the face of external agents (light, inclement weather, washing, permanent waving, perspiration, rubbing).

The dyes should also allow grey hair to be covered, and, lastly, they should be as unselective as possible, that is to say, they should allow the smallest possible colour differences to be obtained along the entire length of the same keratin fiber, which may indeed be differently sensitized (i.e. damaged) between its tip and its root.

Para-phenylenediamine is among the oxidation dye precursors conventionally used to date; it is often combined with ortho-aminophenol (complementary base) and with couplers, including in particular resorcin, and allows deep and intense shades to be obtained.

However, the use of para-phenylenediamine appears recently to have been placed in doubt, in particular for toxicological reasons.

The present invention is directed towards proposing novel compositions for the oxidation dyeing of keratin fibers and in particular human keratin fibers such as the hair, which compositions, although being free of para-phenylenediamine, nevertheless have very good dyeing properties.

Thus, the inventors have discovered that it is possible to obtain novel non-toxic and fast dyes which give rise to intense and quite unselective colours, by combining at least one specific 2-substituted para-phenylenediamine, as defined below, with 3-methyl-6-aminophenol. This discovery forms the basis of the present invention.

The subject of the invention is thus a dye composition for the oxidation dyeing of keratin fibers and in particular human keratin fibers such as the hair, wherein this composition comprises, in a medium which is suitable for dyeing: at least one para-phenylenediamine derivative, as first oxidation base, selected from 2,6-dimethyl-para-phenylenediamine, 2,3-dimethyl-para-phenylenediamine, the para-phenylenediamines of formula (I) below:

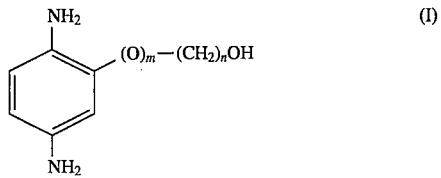

in which m is an integer equal to zero or 1 and n is an integer from 1 to 4 inclusively, and the acid-addition salts thereof, and 3-methyl-6-aminophenol and/or one of the addition salts thereof with an acid, as second oxidation base.

The compositions according to the invention are of low selectivity and the colours obtained moreover display good dyeing power and excellent fastness properties at the same time towards atmospheric agents such as light and inclement weather and towards perspiration and the various treatments to which the hair may be subjected (washing, permanent reshaping operations).

The subject of the invention is also a process for the oxidation dyeing of keratin fibers using this composition.

The acid-addition salts which may be used within the context of the dye compositions of the invention are chosen in particular from the hydrochlorides, the hydrobromides, the sulphates and the tartrates.

Among the para-phenylenediamines of formula (I) above, there may more particularly be mentioned 2-(β-hydroxymethyl)-para-phenylenediamine, 2-(β-hydroxyethyl)-para-phenylenediamine and 2-(β-hydroxyethoxy)-para-phenylenediamine, as well as the salts thereof.

According to a particularly preferred embodiment of the invention, the para-phenylenediamine derivatives are chosen from 2,6-dimethyl-para-phenylenediamine, 2-(β-hydroxyethyl)-para-phenylenediamine and the salts thereof.

All of the oxidation bases in accordance with the invention, that is to say the para-phenylenediamine derivative or derivatives and the 3-methyl-6-aminophenol, together preferably represent approximately from 0.01 to 10% by weight of the total weight of the dye composition, and even more preferably approximately from 0.05 to 5% by weight.

The dye compositions of the invention may also contain at least one coupler chosen from the couplers conventionally employed in oxidation dyeing, and among which there may be mentioned meta-diphenols, meta-aminophenols, meta-phenylenediamines, and heterocyclic compounds such as pyrazolones and indole derivatives.

As examples of couplers which may be used within the context of the present invention, there may more particularly be mentioned resorcin, 2-methylresorcin, meta-aminophenol, 2-methyl-5-aminophenol, 2-methyl-5-N-(β-hydroxyethyl)aminophenol, 2,6-dimethyl-3-aminophenol, 2,4-diamino-1,3-dimethoxybenzene, 2,4-diaminoanisole, 2,4-diaminophenoxyethanol, 2-N-(β-hydroxyethyl)amino-4-aminophenoxyethanol, 2-amino-4-N-(β-hydroxyethyl)aminoanisole, 2,4-diaminophenoxyethylamine, 6-hydroxybenzomorpholine, 6-aminobenzomorpholine, 3,4-methylenedioxyphenol, 3,4-methylenedioxyaniline, 6-hydroxyindole, 7-aminoindole, and the acid-addition salts thereof with an acid.

When they are used, these couplers generally represent approximately from 0.005 to 10% by weight of the total weight of the dye composition, and preferably approximately from 0.01 to 5% by weight.

The dye composition according to the invention may also contain at least one direct dye intended to enrich the shades obtained with glints. These direct dyes may be chosen, for example, from azo dyes, anthraquinone dyes and nitro derivatives from the benzene series.

The appropriate dyeing medium (or support) generally consists of water or of a mixture of water and at least one organic solvent in order to dissolve the compounds which would not be sufficiently soluble in water. By way of organic solvent there may be mentioned, for example, $C_1$–$C_4$ lower alkanols such as ethanol and isopropanol; glycerol; glycols and glycol ethers such as 2-butoxyethanol, propylene glycol, diethylene glycol monoethyl ether and diethylene glycol monomethyl ether, as well as aromatic alcohols such as benzyl alcohol or phenoxyethanol, analogous products and mixtures thereof.

The solvents may be present in proportions preferably approximately from 1 to 40% by weight relative to the total weight of the dye composition, and even more preferably approximately from 5 to 30% by weight.

The pH of the dye composition as defined above is generally from 3 to 11. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkali metal carbonates, alkanolamines such as mono-, di- and triethanolamines as well as the derivatives thereof, sodium hydroxide or potassium hydroxide and the compounds of formula (II) below:

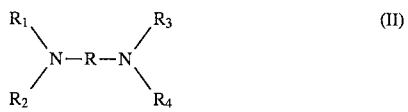

in which R is a propylene residue optionally substituted with a hydroxyl group or a $C_1$–$C_4$ alkyl radical; $R_1$, $R_2$, $R_3$ and $R_4$, which may be identical or different, represent a hydrogen atom, a $C_1$–$C_4$ alkyl radical or a $C_1$–$C_4$ hydroxyalkyl radical.

The dye composition according to the invention may also contain various adjuvants conventionally used in compositions for dyeing the hair, such as anionic, cationic, nonionic, amphoteric and zwitterionic surface-active agents or mixtures thereof, inorganic or organic thickeners, antioxidants, penetration agents, sequestering agents, fragrances, buffers, dispersing agents, conditioning agents, film-forming agents, preserving agents and opacifying agents.

The dye composition according to the invention may be in various forms, such as in the form of liquids, creams or gels, or in any other form which is suitable for dyeing keratin fibers, and in particular human hair.

The subject of the invention is also a process for dyeing keratin fibers, and in particular human keratin fibers such as the hair, using the dye composition as defined above.

According to this process, the dye composition as defined above is applied to the fibers, the colour being developed at acidic, neutral or alkaline pH using an oxidizing agent which is added, only at the time of use, to the dye composition, or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a colour. The mixture obtained is then applied to the keratin fibers and is left to stand for 5 to 40 minutes approximately, preferably for 15 to 30 minutes approximately, after which the fibers are rinsed, washed with shampoo, rinsed again and dried.

The oxidizing agent present in the oxidizing composition as defined above may be chosen from oxidizing agents conventionally used for the oxidation dyeing of keratin fibers, and among which there may be mentioned hydrogen peroxide, urea peroxide, alkali metal bromates, and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibers preferably ranges approximately from 3 to 11 and even more preferably from 5 to 10. It is adjusted to the desired value using acidifying or basifying agents which are usually used in the dyeing of keratin fibers and which are as defined above.

The oxidizing composition as defined above may also contain various adjuvants which are conventionally used in compositions for dyeing the hair and which are as defined above.

The composition which is finally applied to the keratin fibers may be in various forms, such as in the form of liquids, creams or gels, or in any other form which is suitable for dyeing keratin fibers, and in particular human hair.

Another subject of the invention is a multi-compartment dyeing device or "kit" or any other packaging system containing several compartments, a first compartment of which contains the dye composition as defined above, and a second compartment of which contains the oxidizing composition as defined above. These devices may be equipped with a means which makes it possible to deliver the desired mixture onto the hair, such as the devices described in French Patent FR-2,586,913.

The examples which follow are intended to illustrate the invention without, however, limiting the scope thereof.

EXAMPLES

Examples 1 to 6

The following dye compositions were prepared (contents in grams):

| EXAMPLE | 1(*) | 2(*) | 3(*) | 4 | 5(*) | 6 |
|---|---|---|---|---|---|---|
| para-Phenylenediamine | 0.108 | 0.108 | | | | |
| 2-(β-Hydroxyethyl)-para-phenylenediamine dihydrochloride | | | 0.225 | 0.225 | | |
| 2,6-Dimethyl-para-phenylenediamine dihydrochloride | | | | | 0.209 | 0.209 |
| ortho-Aminophenol | 0.436 | | 0.436 | | 0.436 | |
| 3-Methyl-6- | | 0.493 | | 0.493 | | 0.493 |

5 -continued

| EXAMPLE | 1(*) | 2(*) | 3(*) | 4 | 5(*) | 6 |
|---|---|---|---|---|---|---|
| aminophenol | | | | | | |
| Resorcin | 0.550 | 0.550 | 0.550 | 0.550 | 0.550 | 0.550 |
| Common dye support(**) | 60.94 | 60.94 | 60.94 | 60.94 | 60.94 | 60.94 |
| Demineralized water qs | 100 g | 100 g | 100 g | 100 g | 100 g | 100 g |

(*): these dye compositions do not form part of the invention.
(**): Common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl lauryl aminosuccinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Aqueous sodium metabisulphite solution, containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% $NH_3$ | 10.0 g |

At the time of use, each dye composition was mixed weight for weight with an oxidizing composition consisting of a 20-volumes hydrogen peroxide solution (6% by weight) of pH 3. Each resulting mixture was then applied for 30 minutes to a lock of natural grey hair containing 90% white hairs (lock No. 1 of non-sensitized hair), and to a lock of this same grey hair containing 90% white hairs, but which has undergone a permanent-waving operation (lock No. 2 of sensitized hair). The hair was then rinsed, washed with standard shampoo and dried.

The colour of the locks was then evaluated in the Munsell system using a CM 2002 Minolta colorimeter.

According to Munsell notation, a colour is defined by the expression HV/C in which the three parameters respectively denote the shade or Hue (H), the intensity or Value (V) and the purity or Chromaticity (C); the oblique line in this expression is simply a convention and does not indicate a ratio.

The difference in colour between two locks is calculated by applying the Nickerson formula: $\Delta E = 0.4\ Co\Delta H + 6\Delta V + 3\Delta C$, as described, for example, in "Couleur, Industrie et Technique"; pages 14–17 vol. No. 5, 1978.

In this formula, $\Delta E$ represents the difference in colour between two locks, $\Delta H$, $\Delta V$ and $\Delta C$ represent the variation in absolute value of the parameters H, V and C, and Co represents the purity of the lock with reference to which it is desired to evaluate the difference in colour.

The results are given in the Table below:

| EX-AM-PLES | Colour on natural hair | Colour on permanent-waved hair | Difference in colour | | | |
|---|---|---|---|---|---|---|
| | | | ΔH | ΔV | ΔC | ΔE |
| 1(*) | 2.4 Y 3.5/2.3 | 2.9 Y 3.3/2.0 | 0.5 | 0.2 | 0.3 | 2.6 |
| 2(*) | 0.3 Y 3.8/1.9 | 2.4 Y 3.6/2.3 | 2.1 | 0.2 | 0.4 | 4.0 |
| 3(*) | 3.9 Y 4.3/2.8 | 3.9 Y 3.7/2.2 | 0 | 0.6 | 0.6 | 5.4 |
| 4 | 5.3 Y 4.4/2.7 | 5.5 Y 3.9/2.8 | 0.2 | 0.5 | 0.1 | 3.5 |
| 5(*) | 4.0 Y 4.1/2.5 | 3.4 Y 3.5/2.0 | 0.6 | 0.6 | 0.5 | 5.7 |
| 6 | 5.4 Y 4.0/1.8 | 5.7 Y 3.6/2.0 | 0.3 | 0.4 | 0.2 | 3.2 |

(*): Examples not forming part of the invention.

These results show that the compositions in accordance with the invention, although being free of para-phenylenediamine, still have a low selectivity or, at least, an acceptable selectivity.

These results more particularly show that:

1) when para-phenylenediamine is replaced by an oxidation dye precursor in accordance with the invention, such as, for example, 2-(β-hydroxyethyl)-para-phenylenediamine dihydrochloride or 2,6-dimethyl-para-phenylenediamine dihydrochloride, combining it with ortho-aminophenol which does not form part of the invention, an unacceptable increase in the selectivity of the colours obtained is observed (comparison between Examples 1 and 3, or 1 and 5), 2) when in this case ortho-aminophenol is replaced by 3-methyl-6-aminophenol in accordance with the invention but para-phenylenediamine is retained, an unacceptable increase in the selectivity of the colours obtained is also observed (comparison between Examples 1 and 2), 3) when both (i) para-phenylenediamine is replaced by 2-(β-hydroxyethyl)-para-phenylenediamine dihydrochloride or 2,6-dimethyl-para-phenylenediamine dihydrochloride in accordance with the invention, and (ii) ortho-aminophenol is replaced by 3-methyl-6-aminophenol in accordance with the invention, a much smaller increase in the selectivity of the colours obtained is then observed (comparison of Examples 3 and 4, or 5 and 6).

Examples 7 and 8

The following dye compositions in accordance with the invention were prepared (contents in grams):

| EXAMPLE | 7 | 8 |
|---|---|---|
| 2,3-Dimethyl-para-phenylenediamine dihydrochloride | 0.314 | |
| 2-(β-Hydroxyethoxy)-para-phenylenediamine dihydrochloride | | 0.120 |
| 3-Methyl-6-aminophenol | 0.308 | 0.431 |
| 2-Methylresorcin | 0.496 | |
| 2,4-Diaminophenoxyethanol dihydrochloride | | 0.964 |
| Common dye support(*) | 60.94 | 60.94 |
| Demineralized water qs | 100 g | 100 g |

(*)Common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (A.M.) | 5.69 g A.M. |
| Oleic acid | 3.0 g |
| Oleylamine containing 2 mol of ethylene oxide, sold under the trade name Ethomeen O12 by the company Akzo | 7.0 g |
| Diethylaminopropyl | 3.0 g A.M. |

-continued

| EXAMPLE | 7 | 8 |
| --- | --- | --- |
| laurylaminosuccinamate, sodium salt, containing 55% A.M. | | |
| Oleyl alcohol | | 5.0 g |
| Oleic acid diethanolamide | | 12.0 g |
| Propylene glycol | | 3.5 g |
| Ethyl alcohol | | 7.0 g |
| Dipropylene glycol | | 0.5 g |
| Propylene glycol monomethyl ether | | 9.0 g |
| Aqueous sodium metabisulphite solution, containing 35% A.M. | | 0.455 g A.M. |
| Ammonium acetate | | 0.8 g |
| Antioxidant, sequestering agent | | qs |
| Fragrance, preserving agent | | qs |
| Aqueous ammonia containing 20% NH₃ | | 10.0 g |

At the time of use, each dye composition was mixed weight for weight with an oxidizing composition consisting of a 20-volumes hydrogen peroxide solution (6% by weight) of pH 3. Each resulting mixture was then applied for 30 minutes to a lock of natural grey hair containing 90% white hairs. The hair was then rinsed, washed with a standard shampoo and dried.

The dyeing results are given in the Table below:

| EXAMPLE | COLOUR OBTAINED |
| --- | --- |
| 7 | Matt ash-beige |
| 8 | Slightly golden green |

What is claimed is:

1. A dye composition for the oxidation dyeing of keratin fibers, said composition comprising, in a medium which is suitable for dyeing:

at least one first oxidation base or an acid addition salt thereof, said first oxidation base being 2,6-dimethyl-para-phenylenediamine, 2,3-dimethyl-para-phenylenediamine, or a para-phenylenediamine of formula (I):

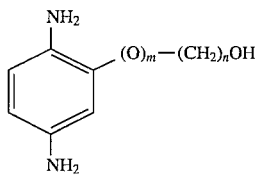

wherein m is an integer equal to zero or 1 and n is an integer ranging from 1 to 4, and at least one second oxidation base, said second oxidation base being 3-methyl-6-aminophenol or an acid-addition salt thereof wherein all of said first and second oxidation bases together represent from 0.01 to 10% by weight of the total weight of the dye composition.

2. The composition according to claim 1, wherein said keratin fibers are human keratin fibers.

3. The composition according to claim 2, wherein said human keratin fibers are hair.

4. The composition according to claim 1, wherein said acid addition salts of said first and second oxidation bases are hydrochlorides, hydrobromides, sulphates and tartrates.

5. The composition according to claim 1, wherein said at least one first oxidation base of formula (I) is 2-(β-hydroxymethyl)-para-phenylenediamine, 2-(β-hydroxyethyl)-para-phenylenediamine, 2-(β-hydroxyethoxy)-para-phenylenediamine, or an acid-addition salt thereof.

6. The composition according to claim 1, wherein said at least one first oxidation base is 2,6-dimethyl-para-phenylenediamine, 2-(β-hydroxyethyl)-para-phenylenediamine, or an acid-addition salt thereof.

7. The composition according to claim 1, wherein all of said first and second oxidation bases together represent from 0.05 to 5% by weight of the total weight of the dye composition.

8. The composition according to claim 1, said composition further comprising at least one coupler, said coupler being a meta-diphenol, a meta-aminophenol, a meta-phenylenediamine, or a heterocyclic coupler.

9. The composition according to claim 8, wherein said heterocyclic coupler is a pyrazolone or an indole.

10. The composition according to claim 8, wherein said at least one coupler is resorcin, 2-methylresercin, meta-aminophenol, 2-methyl-5-aminophenol, 2-methyl-5-N-(β-hydroxyethyl)- aminophenol, 2,6-dimethyl-3-aminophenol, 2,4-diamino-1,3-dimethoxybenzene, 2,4-diaminoanisole, 2,4-diaminophenoxyethanol, 2-N-(β-hydroxyethyl)amino-4-aminophenoxyethanol, 2-amino-4-N-(β-hydroxyethyl)-aminoanisole, 2,4-diaminophenoxyethylamine, 6-hydroxybenzomorpholine, 6-aminobenzomorpholine, 3,4-methylenedioxyphenol, 3,4-methylenedioxyaniline, 6-hydroxyindole, 7-aminoindole, or an acid-addition salt of any of said couplers.

11. The composition according to claim 8, wherein said at least one coupler represents from 0.005 to 10% by weight of the total weight of the dye composition.

12. The composition according to claim 11, wherein said at least one coupler represents from 0.01 to 5% by weight of the total weight of the composition.

13. The composition according to claim 1, said composition further comprising at least one direct dye.

14. The composition according to claim 1, wherein said medium which is suitable for dyeing comprises water or a mixture of water and at least one organic solvent, said solvent being a C1–C4 lower alkanol, glycerol, a glycol, a glycol ether, or an aromatic alcohol.

15. The composition according to claim 1, wherein said composition has a pH from 3 to 11.

16. A process for dyeing keratin fibers comprising the steps of:

applying to said fibers a dye composition as defined in claim 1, and developing colour at acidic, neutral or alkaline pH with an oxidizing agent which is added to the dye composition at the time of applying said dye composition to said fibers, or which is present in an oxidizing composition that is applied to said fibers simultaneously with said dye composition or sequentially to said dye composition.

17. The process according to claim 16, wherein said keratin fibers are human keratin fibers.

18. The process according to claim 17, wherein said human keratin fibers are hair.

19. A multi-compartment dyeing device or "kit" containing at least two compartments, a first compartment of which contains a dye composition as defined in claim 1, and a second compartment of which contains an oxidizing composition.

20. A process for the oxidation dyeing of keratin fibers to lower selectivity thereon, said process comprising the step of dyeing said fibers in a medium suitable for dyeing to lower selectivity on said fibers with a combination of at least one first oxidation base or an acid addition salt thereof, said first oxidation base being 2,6-dimethyl-para-phenylenediamine, 2,3-dimethyl-para-phenylenediamine, or a para-phenylenediamine of formula (I):

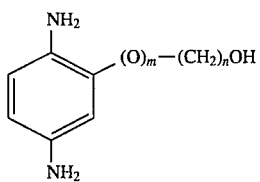 (I)
wherein m is an integer equal to zero or 1 and n is an integer ranging from 1 to 4, and
at least one second oxidation base, said second oxidation base being 3-methyl-6-aminophenol or an acid-addition salt thereof wherein all of said first and second oxidation bases together represent from 0.01 to 10% by weight of the total weight of the dye composition.
* * * * *